United States Patent
Bhardwaj et al.

(10) Patent No.: US 10,145,845 B2
(45) Date of Patent: Dec. 4, 2018

(54) ON-CHIP ASSAY FOR ENVIRONMENTAL SURVEILLANCE

(71) Applicants: Vinay Bhardwaj, Nashville, TN (US); Anthony J. McGoron, Miami, FL (US)

(72) Inventors: Vinay Bhardwaj, Nashville, TN (US); Anthony J. McGoron, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 284 days.

(21) Appl. No.: 14/872,576

(22) Filed: Oct. 1, 2015

(65) Prior Publication Data
US 2017/0097343 A1 Apr. 6, 2017

(51) Int. Cl.
 *G01N 33/543* (2006.01)
 *G01N 33/553* (2006.01)
 *G01N 21/65* (2006.01)
 *G01N 33/68* (2006.01)
 *G01N 33/50* (2006.01)

(52) U.S. Cl.
 CPC ..... *G01N 33/54373* (2013.01); *G01N 21/658* (2013.01); *G01N 33/5014* (2013.01); *G01N 33/54353* (2013.01); *G01N 33/553* (2013.01); *G01N 33/68* (2013.01); *G01N 2201/06113* (2013.01); *G01N 2201/12* (2013.01); *G01N 2333/39* (2013.01)

(58) Field of Classification Search
 CPC ........... G01N 33/54373; G01N 33/553; G01N 33/54353; G01N 33/68; G01N 21/658; G01N 2333/39; G01N 2201/12; G01N 2201/06113
 See application file for complete search history.

(56) References Cited

U.S. PATENT DOCUMENTS 7,518,721 B2  4/2009 Burrell et al.
7,940,387 B2  5/2011 Dluhy et al.

OTHER PUBLICATIONS

Bhardwaj et al. AgNPs-based label-free colloidal SERS nanosensor for the rapid and sensitive detection of stress-proteins expressed in response to environmental-Toxins. J. Biosensors Bioelectronics 2013, Issue S12, pp. 1-7. (Year: 2013).*
Bhardwaj et el. SERS biosensor for label free monitoring of environmental stress. 2013 29th Southern Biomedical Engineering Conference (SBEC), May 3-5, 2013, Publisher IEEE, Miami, FL, USA, INSPEC Accession No. 13564753, pp. 79-80. (Year: 2013).*

(Continued)

*Primary Examiner* — Shafiqul Haq
(74) *Attorney, Agent, or Firm* — Saliwanchik, Lloyd & Eisenschenk (57) ABSTRACT

The subject invention provides methods and means to detect incidents of accidental or intentional release of chemical and biological toxins into the environment by measuring cellular stress-induced proteins in eukaryotic cells exposed to environmental samples suspected of containing chemical or biological toxins using a highly sensitive on-chip surface-enhanced Raman spectroscopy (SERS)-linked immunosensors assay allowing robust, fast, and reliable in-the-field global sensing of environmental threats in resource-limited settings.

11 Claims, 5 Drawing Sheets

(56) References Cited

OTHER PUBLICATIONS

Shachaf et al. A novel method for detection of phosphorylation in single cells by surface enhanced raman scattering (SERS) using composite organic-inorganic nanoparticles (COINs). (Year: 2009).*
Comley, John, "ELISA assays: recent innovations take analyte detection to new levels," *Drug Discovery World*, Fall 2012, pp. 23-45.
Hartigan, Jennifer, et al., "Moving forward with label-free technology," *Drug Discovery World*, Winter 2010/2011, pp. 41-48.
Goolcharan, J., McGoron, A., "SERS Sensor Device for Accurate Detection of Environmental Toxins." Florida International University, Department of Bio-Medical Engineering, 2013, Poster Presentation: Abstract.

* cited by examiner

ON-CHIP ASSAY FOR ENVIRONMENTAL SURVEILLANCE

GOVERNMENT SUPPORT

This invention was made with government support under grant number W81XWH-10-1-0732 awarded by the Department of Defense, U.S. Army Medical Research and Material Command. The government has certain rights in the invention.

BACKGROUND

The increasing threat of an intentional or accidental release of toxins, in particular chemical toxins, including chemical warfare agents (CWAs) and toxic industrial chemicals (TICs) has increased public fear. The major problem in such attacks or accidents is to quickly detect toxins, including unknown toxins. To solve this problem, sensors are needed that are suitable for rapid, inexpensive, simple and effective (RISE) on-site detection in resource-limited settings enabling a comprehensive alert to known as well as unknown toxins.

The present industry standards for detection of chemical toxins are sophisticated analytical chemistry techniques and instruments like mass-spectroscopy (MS), chromatography including liquid or gas (LG/GC) and their combinations (GC-MS, LC-MS etc.). These technologies are accurate, sensitive, and approved by the Environmental Protection Agency (EPA), but they are time-consuming, costly, require well-trained technicians and a laboratory setting, and can only be used to detect known toxins.

Cellular and molecular sensors (biosensors) to detect biomarkers' responses to toxins in genetically-engineered whole cells (bioreporters) and the cellular components such as nucleic acids (polymerase chain reaction, PCR assay) and proteins (enzyme-linked immunosensor assay, ELISA) enable the detection of unknown analytes and toxins, and makes themespecially useful as broad spectrum screening tools and early warning testing methods.

Most biosensor technologies, such as enzyme-linked immunosorbent assay (ELISA), Fluorescence Resonance Energy Transfer (FRET) and bioreporter employing fluorophore dyes (labels), are label-based. Some of the limitations inherent in the use of labels are toxicity, photo bleaching, customized synthesis and conjugation. In addition, label-based sensors introduce uncertainty in measurements as they indirectly determine the concentration of analytes through a signal obtained from label-analyte conjugates.

Whole-Cell Biosensor Technologies that do not use any label (label-free) have also been developed, including Surface Plasmon resonance (SPR), Quartz Crystal Microbalance, Ion-Selective Field Effect Transistor, and Electric Cell-Substrate Impedance Sensing. One major drawback of these technologies is non-specificity.

Generally, cell-based biosensors integrate living cells directly onto the biosensor platform and can incorporate both prokaryotic (bacteria) and eukaryotic (yeast, mammalian) cells. For example, CANARY (Cellular Analysis and Notification of Antigen Risks and Yields) is a technology based on mammalian cells that has recently been developed to create PANTHER (Pathogen Notification for Threatening Environmental Releases) sensors. This system uses mammalian cells that have been transfected to stably express specific antibodies on their surface, which antibodies allow the detection of a variety of pathogens in a short period of time. Due to the use of mammalian cells, which require stringent culture conditions, the CANARY technology has only a short shelf-life of 3 days. Systems such as the CANARY therefore have reduced utility as on-site systems for early detection of biological and chemical warfare or accidental toxin release into the environment.

As an alternative to mammalian cells, yeast cells have previously been used in biosensors. Yeasts are robust single-cell organisms that share close genetic and functional resemblance with human cells. Due to their less demanding culture conditions, yeast cells enable longer shelf-lives of cell-based biosensors, thus allowing broader applicability and on-site utility.

To combine sensitive detection of known and unknown toxins with robust on-site performance, biosensors employing reliable label-free detection technology are needed.

Surface-Enhanced Raman Scattering (SERS) is the best alternative to currently used sensor technologies for monitoring of toxins. The SERS technique is a sensitive and specific tool providing label-free detection of molecules at very low concentrations and allowing the identification of molecules based on their vibrational fingerprint. The SERS effect is based on the optical properties of metal nanoparticle substrates. Upon excitation of the metal nanoparticle substrates by visible light, collective electron oscillations inside the nanoparticles (called localized surface plasmon resonance, LSPR) occur, creating an evanescent wave. The LSPR effect can be measured yielding an extinction spectrum, the maximum of which depends on the nature of the metal, shape and size of the nanoparticles, and the excitation wavelength. In order to achieve the most efficient enhancement, the correct pairing of substrate and excitation laser is critically important. The tuning of nanoparticle size, shape and inter particle spacing is critical to match laser's excitation wavelength towards achieving an ultra-sensitive design.

SERS is employed in two configurations, direct detection of known toxins or the SERS assays to detect nucleic acid or protein biomarkers in response to toxins enabling detection of known as well as unknown toxins.

Cellular proteins involved in stress responses are useful candidates for SERS detection of environmental toxins, because metal nanoparticles can be functionalized with receptors to specific cellular stress proteins and the presence and quantification of such cellular stress proteins in cells exposed to environmental samples are indicative of the presence and concentration of toxins. For example, RAD54 is a key cellular stress protein involved in homologous recombination and DNA repair in many organisms including human and yeast. The RAD54 protein gives a general stress response to all genotoxins and many other diverse classes of toxins, which supports a wide market of the on-chip SLISA developed in this project. A comprehensive screening validation program towards developing a commercial Green-Screen bioreporter assay using Yeast and RAD54 support the global response of our design. Further, exposure-response (ER) relationship curve developed using on-chip SLISA is correlated with EPA's databases on guideline levels of the toxins and risk characterization that will help translation of the information from any toxin, known as well as unknown, allowing global sensing.

BRIEF SUMMARY

The subject invention provides, in preferred embodiments, materials and methods for generating and using an on-chip, yeast-based, label-free, detect-to-protect silver-based surface enhanced Raman spectroscopy (SERS)-linked immunosensor assay (SLISA) for use in chemical and biological sensing applications including, but not limited to, early detection of incidents of accidental or intentional release of chemical and/or biological toxins into the environment, and detection of biomarkers in a variety of disease conditions including, but not limited to, cancer, HIV, neuro-degenerative diseases, diabetes and others.

The SLISA of the subject invention provides key advantages of speed, high accuracy, long shelf-life, and portability, as well as direct, label-free and ultrasensitive detection of known and unknown toxins in resource-limited settings.

DETAILED DESCRIPTION

The subject invention provides, in preferred embodiments, materials and methods of generating and using an on-chip, yeast-based, label-free, detect-to-protect silver-based surface enhanced Raman spectroscopy (SERS)-linked immuno-sensor assay (SLISA) intended for use by, for example, first responders in the early detection of incidents of accidental or intentional release of chemical and biological toxins into the environment.

In particular embodiments, the SLISA of the subject invention fulfills the requirements of a rapid, inexpensive, simple and effective (RISE) detect-to-protect portable biosensing that is needed for civilian protection in incidents of chemical and biological toxin release. In alternative embodiments, the SLISA of the subject invention provides rapid and robust detection of biomarkers for bed-site monitoring of diseases including, but not limited to, cancer, HIV, diabetes, and neuro-degenerative diseases.

The SLISA of the subject invention provides accuracy similar to traditional techniques including ELISA, PCR and chromatography, while outperforming these prior techniques by fulfilling the RISE requirements of a portable device to be used by first responders in resource-limited settings.

In preferred embodiments, the subject invention provides an on-chip SLISA for detection of known and unknown toxins in an environmental sample, the assay comprising:
(a) a housing, having at least two compartments;
(b) cells to be housed in at least one of the compartments, which cells are to be exposed to the environmental sample;
(c) SERS-linked immunosensors, which are to be contacted with the cells, the immunosensors comprising:
  i. a metallic core;
  ii. linker molecules connecting the metallic core to
  iii. antibodies to at least one cellular biomolecule;
(d) a Raman spectrometer;
(e) a data processing module in operable communication with the Raman spectrometer;
(f) an algorithm contained within the data processing module that determines the presence and, optionally, the concentration of one or more toxins in the environmental sample based on the amount of cellular biomolecules detected;
(g) a display in operable communication with the data processing module; and, wherein in operation,
(h) an indication communicated to the display from the data processing module indicating the presence and/or concentration of at least one toxin present in the environmental sample.

In particular embodiments, the SLISA of the subject invention provides a poly-methyl methacrylate (PMMA)-based microchip with a glass bottom that is easily machined, provides suitable mechanical properties, and is characterized by minimum Raman background signals.

In specific embodiments, the glass-bottom SLISA microchip of the subject invention houses at least two compartments or wells, has a step around the perimeter of the top to fit a lid and a step at the bottom to avoid contact of the glass bottom with the underlying surface.

In some embodiments the SLISA microchip of the subject invention is of a size suitable for use with commercial coverslips. In other embodiments, the SLISA microchip of the subject invention is of suitable dimensions to be used with a Raman spectro-microscope. In yet other embodiments, the SLISA microchip of the subject invention is of any dimension suitable to use with a hand-held point-and-shoot Raman spectrometer.

In preferred embodiments, the glass-bottom SLISA microchip of the subject invention provides multiple compartments or wells for the simultaneous performance of multiple tests and/or high throughput screening. In other preferred embodiments, the glass-bottom SLISA microchip is reusable.

In particular embodiments, the SLISA of the subject invention provides methods and means to detect incidents of accidental or intentional release of chemical and/or biological toxins into the environment by measuring cellular stress-induced proteins in eukaryotic cells exposed to environmental samples suspected of containing chemical and/or biological toxins using highly sensitive SERS-linked immuno-sensors and Raman spectroscopy allowing robust, fast, and reliable in-the-field sensing of environmental threats.

In specific embodiments, the subject invention provides an on-chip SLISA for detection of known and unknown toxins in an environmental sample, the assay comprising:
(i) a housing, having at least two compartments, a glass bottom, a step at the bottom to prevent contact of the glass bottom with the underlying surface, and a lid;
(j) cells to be housed in at least one of the compartments, which cells are to be exposed to the environmental sample;
(k) SERS-linked immunosensors, which are added to the cells, or cell lysate, the immunosensors having:
  i. a metallic core;
  ii. bifunctional linker molecules connecting the metallic core, and
  iii. antibodies to at least one cellular biomolecule;
(l) a Raman spectrometer contacting the glass bottom of the housing and detecting surface-enhanced Raman scattering resulting from the interaction of the cellular biomolecules with the SERS-linked immunosensors;
(m) a data processing module in operable communication with the Raman spectrometer;
(n) an algorithm contained within the data processing module that determines the presence and, optionally, the concentration of known and unknown toxins in the environmental sample based on the amount of cellular biomolecules detected in the cell lysate;
(o) a display in operable communication with the data processing module; and, wherein in operation,
(p) an indication communicated to the display from the data processing module including the presence and concentration of known or unknown toxins present in the environmental sample.

In specific embodiments, the SLISA of the subject invention utilizes eukaryotic cells as sensor organisms. For example, the SLISA of the subject invention can utilize mammalian cells as sensor organisms. In preferred embodiments the SLISA of the subject invention utilizes yeast cells, which share close genetic and functional resemblance to human cells and are cultured under less stringent culture conditions than, for example, mammalian cells, as sensor organisms thus enhancing the shelf-life of the SLISA compared to mammalian cell-based assays.

In particular embodiments, the subject invention provides SERS-linked immunosensors made from silver-colloidal nanoparticles (AgNPs), which AgNPs are matched in their particular shape, size, charge and concentration to the excitation wavelength of the Raman spectrometer used in performing the SLISA, thus optimizing Raman signal efficiency.

In preferred embodiments, the AgNPs of the subject invention are functionalized with antibodies to cellular biomolecules. In specific embodiments, the cellular biomolecules are cellular proteins. In preferred embodiments, the cellular proteins are stress-induced proteins. In most preferred embodiments, the cellular stress proteins are RAD54 proteins.

In particular embodiments, the subject invention provides methods for conjugating antibodies to AgNP via bifunctional linker molecules, which methods mitigate potential AgNP-related toxicity and increase yields of AgNP-antibody conjugation. In specific embodiments, the linker molecules covalently bind to the AgNPs via metal-sulphur bonds and to the antibodies via peptide bonds. In further embodiments, the methods provided by the subject invention ensure dense surface coverage of AgNPs with antibodies, low agglomeration of sensors, and minimal cell toxicity of antibody-coated AgNP immunosensors due to minimal oxidation and dissolution to ionic silver.

In preferred embodiments, the subject invention provides means to detect the interaction of cellular proteins, such as RAD54, with AgNP-immobilized antibodies, by detecting the close proximity to the AgNP surface of antibody-binding epitopes of the RAD54 protein, which epitopes are rich in aliphatic amino acids, leading to characteristic increases in Raman signals specific for aliphatic amino acids.

In other embodiments, the subject invention provides for the quantification of unspecific or background binding of cellular proteins, such as RAD54, to the naked AgNP surface, by detecting the close proximity to the AgNP surface of RAD54 amino acids outside the antigen-binding epitope, which amino acids are rich in aromatic amino acids, leading to characteristic increases in Raman signals specific for aromatic amino acids.

In preferred embodiments, the kinetics of RAD54 interactions with antibodies on AgNPs are determined by detecting the RAD54 protein reorientation relative to the AgNP surface as measured by decreased detection of aromatic amino acid signals (representing direct RAD54-AgNP contact) and increased detection of aliphatic amino acid signals (representing the specific interaction of RAD54 protein with AgNP-bound anti-RAD54 antibodies).

Therefore, in certain embodiments, in addition to detecting and quantifying specific antibody-antigen interactions, the SERS-linked immunosensors of the subject invention detect and quantify unspecific interactions of antigen with the naked AgNP substrate thus allowing enhanced sensitivity and specificity compared to traditional label-mediated detection methods.

The SLISA of the subject invention provides higher efficiency than conventional ELISA-based methods for detection of cellular proteins, because the SLISA of the subject invention requires only a single antigen-antibody binding event, no washing steps, no label, and the compartments or wells of the glass-bottom microchip of the subject invention are reusable.

In particular embodiments, the SLISA of the subject invention provides means for the detection of stress-induced cellular proteins or stress proteins, including, but not limited to, RAD54 proteins, heat shock proteins (HSP), ADAMTS1, Bcl-2, Carbonic Anhydrase IX, Cited-2, COX-2, Cytochrome c, Dkk-4, FABP1/L-FABP, HIF-1 alpha, HIF-2 alpha, Phospho-HSP27, HSP-60, HSp-70, IDO, Phospho-JNK Pan, NFkappaB1, p21/CIP, p27/Kip1, Phospho-p38 alpha, Phospho-p53, PON1, PON2, PON3, Thioredoxin-1, SIRT2, and SOD2.

"Toxins" include any substance that is harmful to the natural function of a cell and/or organism, wherein the cell originates from organisms including, but not limited to, mammals.

In specific embodiments, the SLISA of the subject invention provides methods for detection of target proteins in intact cells. In some embodiments, the SERS-linked immunosensors are delivered into cells by active delivery using electroporation. In other embodiments, the SERS-linked immunosensors are delivered into intact cells using cell-penetrating peptides conjugated to the immunosensors. In preferred embodiments, the cell-penetrating peptides are derived from a cell permeable HIV Trans-Activator of Transcription (TAT) protein transduction domain connected to amino acids 1-20 of influenza A virus hemagglutinin (HA2) protein (TAT-HA2). In other embodiments, the cell-penetrating peptides include, but are not limited to, MAP, Penetratin-Arg, anti-trypsin, Temporin L, Maurocalcine, Cadherin-5, Calicitonin, Neurturin, Human P1, Penetratin, and Pep-1-Cysteamine.

In particular embodiments, the SERS-linked immunosensors are comprised of spherical, or almost spherical, AgNPs. In some embodiments, the AgNPs are 20 nm, 25 nm, 30 nm, 35 nm, 40 nm, 45 nm, 50 nm, 55 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, or 140 nm in diameter, or any diameter in between these diameters. In preferred embodiments, the AgNPs of the SERS-linked immuno-sensors of the subject invention measure roughly 55 to 65, or 60, nanometers in diameter to achieve a preferred SERS signal enhancement and efficient cellular uptake.

In some embodiments, the SERS-linked immunosensors of the subject invention have a core made from a metal including, but not limited to, silver, gold, copper, platinum, or palladium.

In preferred embodiments, the average SERS Enhancement Factor of the AgNPs of the subject invention is more than $3.0 \times 10^5$, $4.0 \times 10^5$ or $4.5 \times 10^5$. In some embodiments, the enhancement by the SERS substrate is further increased by patterning substrates in a highly ordered arrangement (array) or using aggregating agents. In yet other embodiments, the SERS-linked immunosensors are colloidal and used for intracellular application.

In one embodiment the environmental sample is selected from the group consisting of air, water, soil, industrial waste streams, samples collected from surfaces, and biological samples from plants and animals.

The subject invention provides RAD54-based SERS-linked immunosensors, which are highly sensitive due to the high number of SERS active aromatic amino acids and the large molecule size of RAD54 leading to high Raman activity. The high signal-to-noise ratio of the RAD54-based SLISA of the subject invention allows acquisition of intense SERS signals and enables Raman signal detection on SLISA microchips using a hand-held point-and-shoot Raman spectrometer. The subject invention further provides a yeast cell-based SLISA having an extended shelf-life and enabling the use of the subject invention as an on-chip device for in-the-field early detection of environmental toxins.

Following are examples that illustrate procedures and embodiments for practicing the invention. The examples should not be construed as limiting.

EXAMPLES

Example 1—Fabrication of Reusable, Glass-Bottom Microchips

Poly-methyl methacrylate (PMMA), common name plexiglass, is the choice of material to fabricate microchip (2×3 wells) to perform 3 tests in one experiment. The plexiglass is preferred over polystyrene, which is commonly used to fabricate commercial well plates, as the plexiglass is easily machined and has almost double strength (yield strength: 80 vs 50 MPa).

The dimensions of the microplate were 30.5×25.5×1 mm (L×W×H) with a 3 mm step around the perimeter of the top to fit a lid. These dimensions were chosen in reference to rectangular glass coverslip (30×25 mm), which is generally used to cover microscope slide samples.

The microchip with glass bottom gives minimum Raman background signals and the use of commercial coverslips decreases the cost of the microchip. The step at the bottom prevents contact of the glass bottom with the underlying surface, avoiding any chances of physical damage.

Figure 1:
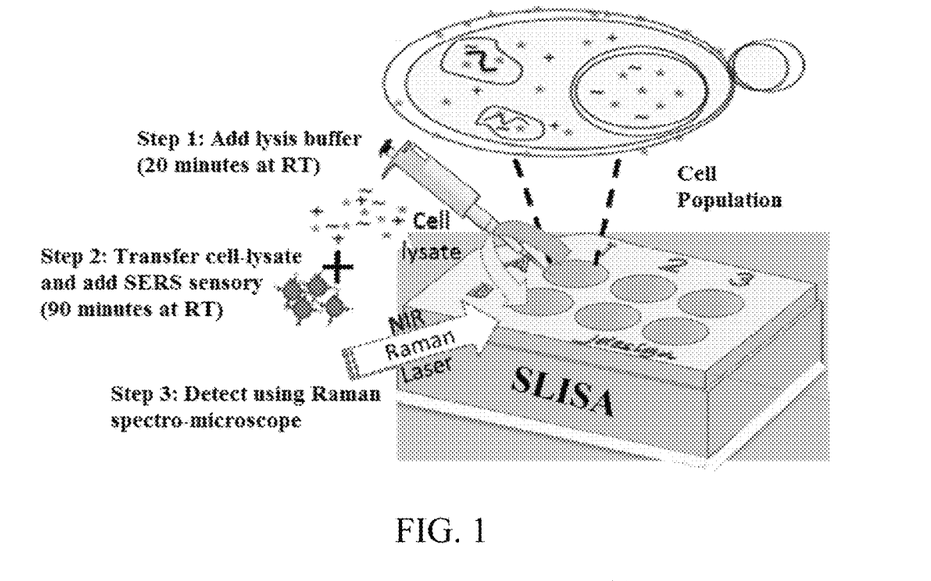
FIG. 1 shows a schematic of a lab-on-a-chip SERS-linked immunosensor assay (LOC-SLISA).

FIG. 1 shows the design of the microchip and the schematic of the on-chip SERS-linked immunosensor assay. The microchip was found to have no toxic effect on yeast growth and to have negligible Raman background signals compared to polystyrene.

Example 2—Exposure Studies Using Yeast Cells

Yeast cells grown in YPD (for Yeast-extract, Peptone and Dextrose culture medium) was harvested in early saturation phase of growth and distributed into the first row of the microchip (A1 through A3), covered with a plexiglass lid and stored as slurries ($10^7$ cells) at 4° C. until use. $H_2O_2$ was added to experimental wells and deionized water to the control well.

A single time, multiple dose study was done at 170, 1700 and 17,000 ppm for 60 minutes. Y-PER (for Yeast-Protein Extraction Reagent) supplemented with protease inhibitor cocktail was added to the cells and incubated for 20 minutes at room temperature (RT).

The supernatant (cell extract) was transferred using an ultrafine pipette tip to the second row of wells (B1 through B3) and incubated with the colloidal SERS immunosensor for RAD54 detection by incubating for 90 minutes at RT.

Example 3—SERS Spectral Acquisition and Analysis

SERS spectra were acquired by Raman Spectro-microscope (Raman station 400F and microscope 300 from Perkin Elmer) using Spectrum software. The number of spectra per sample was 10 and spectral acquisition, number×time of exposure was 2×3 sec. Spectral pre-processing, including background subtraction, baseline correction and compression was done using the built-in Spectrum software.

The spectra were analyzed by multivariate PCA-LDA (principle component analysis and linear discriminant analysis) using the leave-one-out cross validation model. The levels of RAD54 protein were measured using the SERS-linked immunosensor assay and RAD54 levels expressed in response to $H_2O_2$ were correlated to EPA 3-tier guideline levels, IDLHs (for Immediately Dangerous to Life and Health concentrations) as determined by the Center for Disease Control and Prevention (CDC).

Example 4—Synthesis and Characterization of SERS Immunosensors

Colloidal AgNPs were synthesized using the conventional citrate reduction method and monoclonal antibodies (MAbs) specific for RAD54 protein were conjugated to AgNPs via traditional carbodiimide chemistry. Some modifications to mitigate AgNPs-specific toxicity and increase yield of MAb conjugation to AgNPs (SERS immuno-sensor) were implemented (Bhardwaj, V., Srinivasan, S. and McGoron, A. J., "AgNPs-based label-free colloidal SERS nanosensor for rapid and label-free detection of stress-proteins expressed in response to environmental-toxins," J. Biosens. Bioelectron. S12, pp 7 (2013)).

Figure 2A:
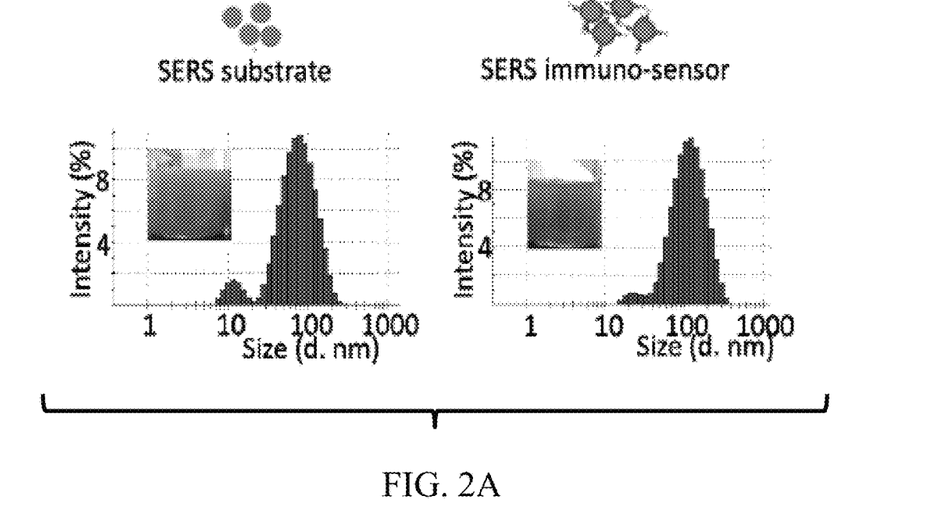
FIGS. 2A-2B depict the physical characterization of silver nanoparticle (AgNP)-based SERS substrate (left column) and immunosensor for RAD54 detection (right column). (2A) Characteristic color change (inset images) and increase in average size (histogram) of SERS substrate after antibody conjugation (immunosensor) is observed. (2B) Transmission electron microscopy (TEM) images of base AgNPs (SERS substrate, left) and RAD54 antibody (white dots/filaments, right) conjugated AgNPs (immune-sensor).
Figure 2B:
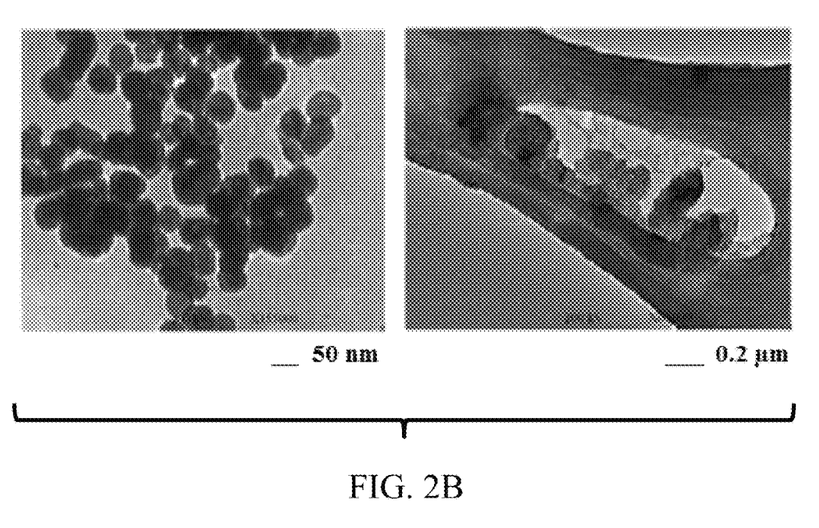
Figure 3:
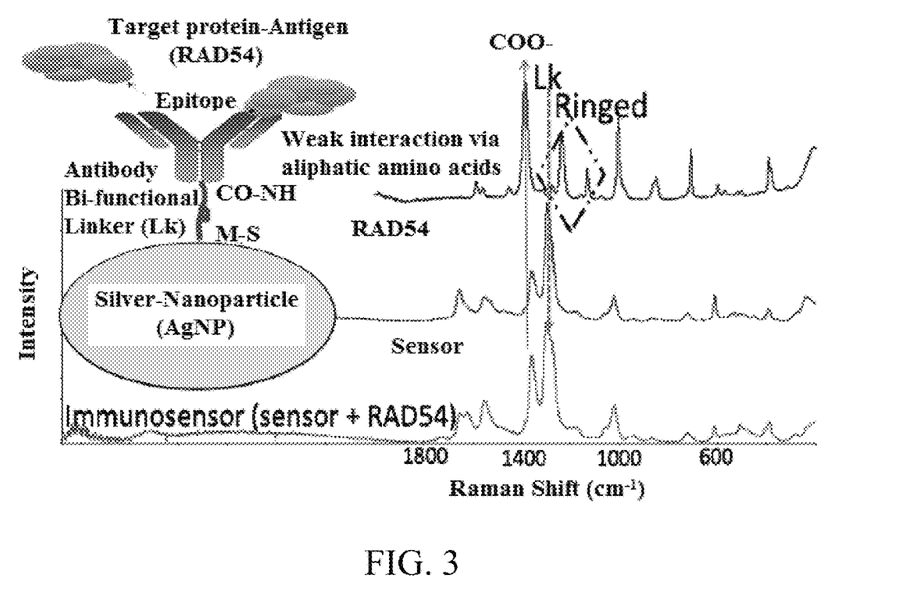
FIG. 3 depicts the chemical characterization and qualitative information on SERS immunosensing (antigen-antibody interaction). The schematic (left) shows the SERS immunosensing. The characteristic SERS spectra (right) give the qualitative information on immunosensing. The bi-functional linker (Lk with SH and COOH groups at the end) covalently binds to the AgNP via a metal-sulphur (M-S) bond and to the antibody via a peptide bond (CO—NH). The spectra characteristic to ring containing aromatic amino acids are dominant in direct SERS of the RAD54 protein, but disappear in the immunosensor. The Lk band at ~1280 $cm^{-1}$ serves as internal standard.

FIGS. 2 and 3 show the physical and chemical characterization of the SERS immunosensor. Almost spherical AgNPs of roughly 60 nanometer diameter were fabricated (FIG. 2), as this is the best size to achieve high SERS signal enhancement and cellular uptake (Stamplecoskie, K. G., Scaiano, J. C., Tiwari, V. S. and Anis, H., "Optimal size of silver nanoparticles for surface enhanced Raman spectroscopy," J. Phys. Chem. C 115(5), 1403-1409 (2011); Chithrani, B. D., Ghazani, A. A. and Chan, W. C., "Determining the size and shape dependence of gold nanoparticle uptake into mammalian cells," Nano Lett. 6(4), 662-668 (2006)).

As compared to ELISA, the SERS-linked immunosensor assay gives qualitative information on the immunosensor, i.e., synthesis, and qualitative and quantitative information on binding of antigen to antibody (immunosensing) (FIG. 3).

Specifically, the MAb binding region of RAD54 protein (epitope) is rich in aliphatic amino acids and therefore an intensity increase around 1390 cm$^{-1}$, characteristic to the carboxylic group (acidic amino acids), is observed upon antigen-antibody interaction. In direct SERS of RAD54 protein the aromatic amino acids (ringed structure) closely interact with AgNPs, giving strong signals. However, the interaction of RAD54 protein with the SERS sensor (antigen-antibody interaction) occurs via the aliphatic region and moves the aromatic amino acids away from the AgNPs, decreasing the characteristic peaks.

Example 5—Comparison of SERS-Linked Immunosensor Assay and ELISA

Figure 4:
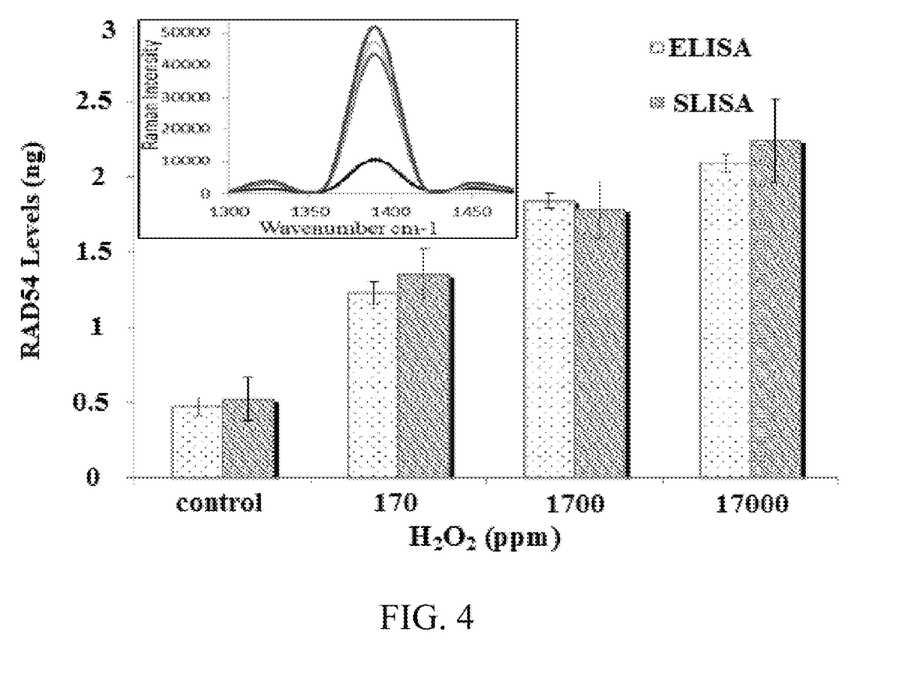
FIG. 4 shows the correlation in accuracy of the SERS-linked immunosensor assay (SLISA) and ELISA for the detection of RAD54 protein expressed in a dose dependent response to $H_2O_2$ toxin. The inset shows the dose dependent increase in the carboxylic band at 1390 $cm^{-1}$, which was used to quantify RAD54 levels using the SERS-linked immunosensor assay.

The carboxylic groups (COO—) band at ~1390 cm$^{-1}$ is qualitatively as well as quantitatively distinct in the immunosensor and therefore was considered for the quantification of RAD54 protein levels expressed in response to $H_2O_2$ toxin (FIG. 4). A dose-dependent increase in peak intensity of protein measured at 1390 cm$^{-1}$ was observed (FIG. 4, inset). The accuracy of protein detection in response to toxin correlated well between SLISA and ELISA (FIG. 4) and about a 4-fold increase in RAD54 expression in response to $H_2O_2$ was observed as compared to control (baseline expression by cells with no toxin exposure).

A performance comparison between SLISA and ELISA with regard to parameters (Table 1) revealed that the SLISA outperformed ELISA in being simple, rapid, reusable, sensitive, and time and labor cost-efficient.

improve the reproducibility of SLISA. However, flexibility of colloidal substrates allows wider applications including live-cell SERS immunosensor for intracellular detection of proteins. In contrast to ELISA, SLISA gives information on immunosensing, including qualitative information on the synthesis, stability, and antigen-antibody interaction. Furthermore, SLISA is more sensitive than ELISA with a lower limit of detection (Table 1).

Example 6—Translation of $H_2O_2$/RAD54-Dose/Effect Relationship to IDLHs

The EPA, in alliance with other federal agencies, is working on a global initiative to establish the exposure limits of toxins for use by the general public and first responders to control emergency situations. Indeed, they have developed several tools and databases for the same: including provisional advisory levels (PALs) in support for environmental rapid risk assessment (SERRA), acute exposure guideline levels (AEGLs) by office of pollution prevention and toxics (OPPT), immediately dangerous to life or health concentration (IDLHs) by agency for toxic substances and disease registry (ATSDR) and the Centers for Disease Control and Prevention (CDC).

Figure 5:
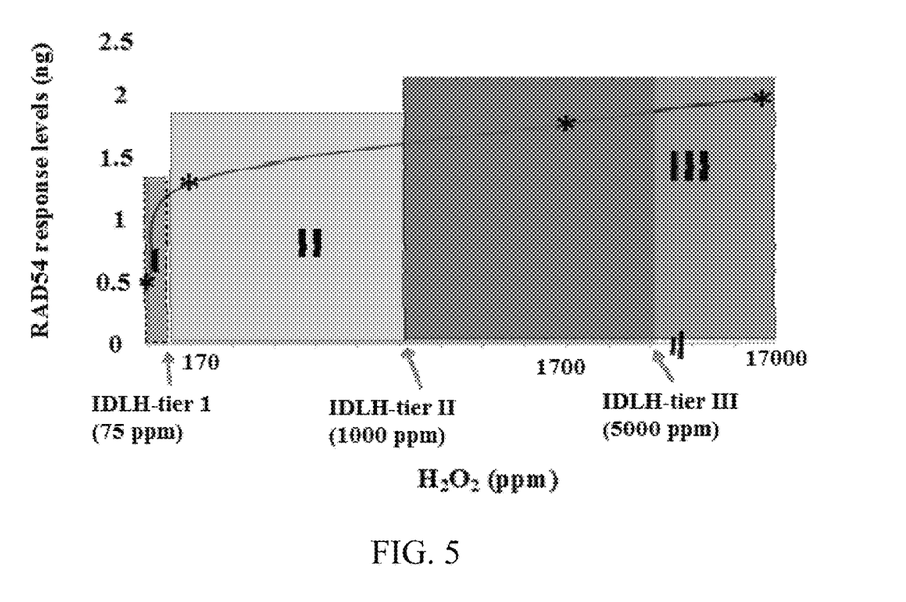
FIG. 5 shows the translation of dose/effect or exposure-response relationship ($H_2O_2$ stress-toxin/RAD54 stress-protein) to 3-tiered levels of IDLHs (for Immediately Dangerous to Life and Health concentrations) defined by EPA-ATSDR-CDC. The color code indicates the severity of the health-effect of toxin levels.

Hydrogen peroxide is a choice of model toxin as it is well characterized for its toxicity mechanisms/pathway and is listed in AEGLs and IDLHs priority list of chemical toxins. Three tiered IDLHs of $H_2O_2$ are drafted: tier I (tolerable, transient health effect)≤75 ppm, tier II (lethal, long-lasting disabling effect)≤1000 ppm, tier III (lethal, life-threatening effect or even death)>1000 ppm and the recommended exposure limit (REL) is 1 ppm (FIG. 5). Up to 5000 ppm dose of $H_2O_2$ has been reported to be tolerated by organisms; therefore the tier II dose might be revised in the near future. The RAD54 protein gives a general stress response to almost all toxins and therefore the dose/effect relationship curve can be used to translate the information from any toxin, known as well as unknown, allowing global sensing.

The on-chip SERS-linked immune biosensor outperformed traditional ELISA in being RISE towards developing a detect-to-protect biosensor for applications in resource-

TABLE 1

| Performance comparison (RISE): ELISA vs SLISA | | | | | |
|---|---|---|---|---|---|
| | Rapid | Inexpensive | | Simple | Effective | |
| | Time (hrs) | Well-plate | Reagents | #Steps | Qualitative | Quantitative |
| ELISA | ≥6 | Not reusable Wells pre-coated with antibodies | Primary & Secondary Ab Enzyme, Substrate & Label #1 each | ≥7 Several washings | Label-Based Indirect Detection | LOD: 50 pg/ml $R^2$: 0.99 |
| SLISA | ≤2 | Reusable | Primary MAb No need of Enzyme, Substrate & Label | ≤3 No washing | Label-Free Direct Detection | LOD: 10 pg/ml $R^2$: 0.97 |

In addition, the SLISA allows label-free detection to avoid uncertainty associated with a label, e.g., fluorescent/absorption tags used in ELISA.

Controlling geometry and inter-particle distance of the SERS substrate by, for example, using lithography, can limited settings. The SERS-linked immunosensor outperformed the ELISA by allowing direct label-free detection and gave qualitative information on the immunosensor, including the synthesis, stability and antigen-antibody interaction. The reproducibility of SERS was achieved by controlling geometry, and inter-particle distance between SERS substrate using lithography (Lin, X. M., Cui, Y., Xu, Y. H., Ren, B., and Tian, Z. Q., "Surface-enhanced Raman spectroscopy: substrate-related issues" Anal. Bioanal. Chem. 394(7), 1729-1745 (2009); Lee, M., Lee, S., Lee, J. H., Lim, H. W., Seong, G. H., Lee, E. K., Chang, S. L., Oh, C. H. and Choo, J., "Highly reproducible immunoassay of cancer marker on a gold-patterned microarray chip using surface-enhanced Raman scattering imaging" 26(5), 2135-2141 (2011)).

The integration of label-free, cell-based immunosensing offers the best combination of their inherent strengths to develop a biomedical and environmental sensor technology, which requires RISE detect-to-protect sensing, in particular needed for rapid, direct and continuous monitoring of the health of human and environment.

It should be understood that the examples and embodiments described herein are for illustrative purposes only and that various modifications or changes in light thereof will be suggested to persons skilled in the art and are to be included within the spirit and purview of this application.

What is claimed is:

1. An on-chip surface-enhanced Raman spectroscopy (SERS)-linked immune biosensor to detect a toxin in an environmental sample, the biosensor comprising:
a housing having a top, a bottom, multiple compartments, and a rectangular glass cover slip, wherein the top has a step around the perimeter to fit the rectangular glass coverslip, the bottom is a glass bottom, and the multiple compartments are fabricated from poly-methyl methacrylate (PMMA);
wherein in separate compartments of the housing:
at least one of the compartments houses cells, which cells are to be exposed to the environmental sample;
at least one of the compartments contains a metallic core SERS substrate prepared from chemicals consisting of silver nitrate salt and sodium citrate, and
at least one of the compartments contains SERS-linked immunosensors comprising:
i) the metallic core SERS substrate;
ii) a linker molecules covalently linked to the metallic core SERS substrate; and
iii) an antibody to at least one cellular biomolecule covalently linked to the linker molecule, wherein the cellular biomolecule is a stress-induced cellular RAD54 protein.

2. The biosensor according to claim 1, wherein the metallic core SERS substrate comprises a metal selected from the group consisting of silver, gold, copper, platinum, and palladium.

3. The biosensor according to claim 2, wherein the metallic core SERS substrate is silver.

4. The biosensor according to claim 1, wherein the SERS-linked immunosensors are spherical or almost spherical.

5. The biosensor according to claim 1, wherein the SERS-linked immunosensors are from 30 nm to 90 nm in diameter.

6. The biosensor according to claim 5, wherein the SERS-linked immunosensors are 60 nm in diameter.

7. The biosensor according to claim 1, comprising antibodies to at least two cellular biomolecules.

8. An on-chip surface-enhanced Raman spectroscopy (SERS)-linked immune biosensor to detect a toxin in an environmental sample, the biosensor comprising:
a housing having a top, a bottom, multiple compartments, and a rectangular glass cover slip, wherein the top has a step around the perimeter to fit the rectangular glass coverslip, the bottom is a glass bottom, and the multiple compartments are fabricated from poly-methyl methacrylate (PMMA);
wherein in separate compartments of the housing:
at least one of the compartments houses cells, which cells are to be exposed to the environmental sample;
at least one of the compartments contains a metallic core SERS substrate prepared from chemicals consisting of silver nitrate salt and sodium citrate, and
at least one of the compartments contains SERS-linked immunosensors comprising:
i) the metallic core SERS substrate;
ii) a linker molecules covalently linked to the metallic core SERS substrate; and
iii) an antibody to at least one cellular biomolecule covalently linked to the linker molecule, wherein the cellular biomolecule is a stress-induced cellular protein selected from the group consisting of heat shock protein (HSP), ADAMTS1, Bcl-2, Carbonic Anhydrase IX, Cited-2, COX-2, Cytochrome c, Dkk-4, FABP1/L-FABP, HIF-1 alpha, HIF-2 alpha, Phospho-HSP27, HSP-60, HSP-70, IDO, Phospho-JNK Pan, NFkappaB1, p21/CIP, p27/Kip1, Phospho-p38 alpha, Phospho-p53, PON1, PON2, PON3, Thioredoxin-1, SIRT2, and SOD2.

9. The biosensor according to claim 1, wherein the SERS-linked immunosensors further comprise: (iv) a cell permeability peptide conjugated to the metallic core SERS substrate;
wherein the cell permeability peptide facilitates efficient uptake of the SERS-linked immunosensors by the cells.

10. The biosensor according to claim 9, wherein the cell permeability peptide is TAT-HA2, MAP, Penetratin-Arg, anti-trypsin, Temporin L, Maurocalcine, Cadherin-5, Calicitonin, Neurturin, Human P1, Penetratin, or Pep-1-Cysteamine.

11. The biosensor according to claim 1,
wherein the glass bottom of the housing has a step to prevent contact of the glass bottom with the underlying surface.

* * * * *